United States Patent [19]
Nair et al.

[11] Patent Number: 5,691,275
[45] Date of Patent: Nov. 25, 1997

[54] ALKALI METAL FORMONONETIN AND METHOD OF MYCORRHIZAL STIMULATION

[75] Inventors: Muraleedharan G. Nair, Okemos; Gene R. Safir, East Lansing; Robert E. Schutzki, Eaton Rapids; Brendan A. Niemira, East Lansing, all of Mich.

[73] Assignee: Board of Trustees operating Michigan State University, East Lansing, Mich.

[21] Appl. No.: 593,265

[22] Filed: Jan. 29, 1996

[51] Int. Cl.$^6$ .................. A01N 43/16; A01N 63/04; C07D 311/36; C12N 1/14
[52] U.S. Cl. .................. 504/108; 504/292; 504/117; 549/403; 435/254.1; 435/256.6
[58] Field of Search ............... 549/403; 504/292, 504/117, 108; 435/254.1, 256.6

[56] References Cited

U.S. PATENT DOCUMENTS

| | | | |
|---|---|---|---|
| 5,002,603 | 3/1991 | Safir et al. | 71/88 |
| 5,085,682 | 2/1992 | Safir et al. | 71/88 |
| 5,125,955 | 6/1992 | Safir et al. | 71/88 |
| 5,399,558 | 3/1995 | Baker et al. | 514/232.5 |

OTHER PUBLICATIONS

Phillips, J.M. and D.S. Hayman, Trans. Brit. Mycol. Soc. 55:158–161 (1970).

Kormanik, P.P. and A.C. McGraw, Quantification of vesicular-arbuscular mycorrhizae in plant roots, in: N.C. Schenck (ed.) Methods and principles of mycorrhizal research. APS Press, St. Paul, MN pp.37–45 (1982).

*Primary Examiner*—S. Mark Clardy
*Attorney, Agent, or Firm*—Ian C. McLeod

[57] ABSTRACT

Compositions of an alkali metal formononetinate, particularly potassium and sodium, for stimulating the growth of mycorrhizal fungi which colonize the plant and in turn stimulate growth of the plant. The results are improved over formononetin.

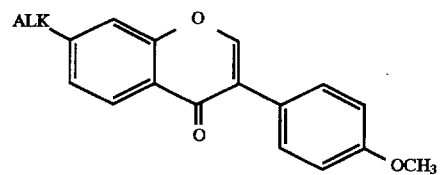

ALK = K, Na

30 Claims, 2 Drawing Sheets

ALKALI METAL FORMONONETIN AND METHOD OF MYCORRHIZAL STIMULATION

BACKGROUND OF THE INVENTION (1) Summary of the Invention

The present invention relates to a method and compositions for use in stimulating mycorrhizal fungi (Mycorrhizae) using an alkali metal formononetinate. In particular, the present invention relates to a method which provides improved results over formononetin.

(2) Description of Related Art

U.S. Pat. Nos. 5,002,603, 5,085,682 and 5,125,955 describe the use of formononetin, an isoflavonoid, as a stimulant for the growth for vesicular arbuscular mycorrhizal fungi. This compound is insoluble in water and is thus less readily available to the fungi. Formulation of formononetin with methanol and water is not commercially viable because of the large volumes of water necessary to solubilize it. There is a need for a formulation of a formononetin derivative which can be used commercially.

OBJECTS

It is therefore an object of the present invention to provide a water soluble compound derived from formononetin which can be easily applied to the fungi and/or the plants. Further, it is an object of the present invention to provide a method which reduces the amount of water necessary to apply water soluble compound and which is commercially economical. These and other objects will become increasingly apparent by reference to the following description and the drawings.

DESCRIPTION OF PREFERRED EMBODIMENTS

Figure 1:
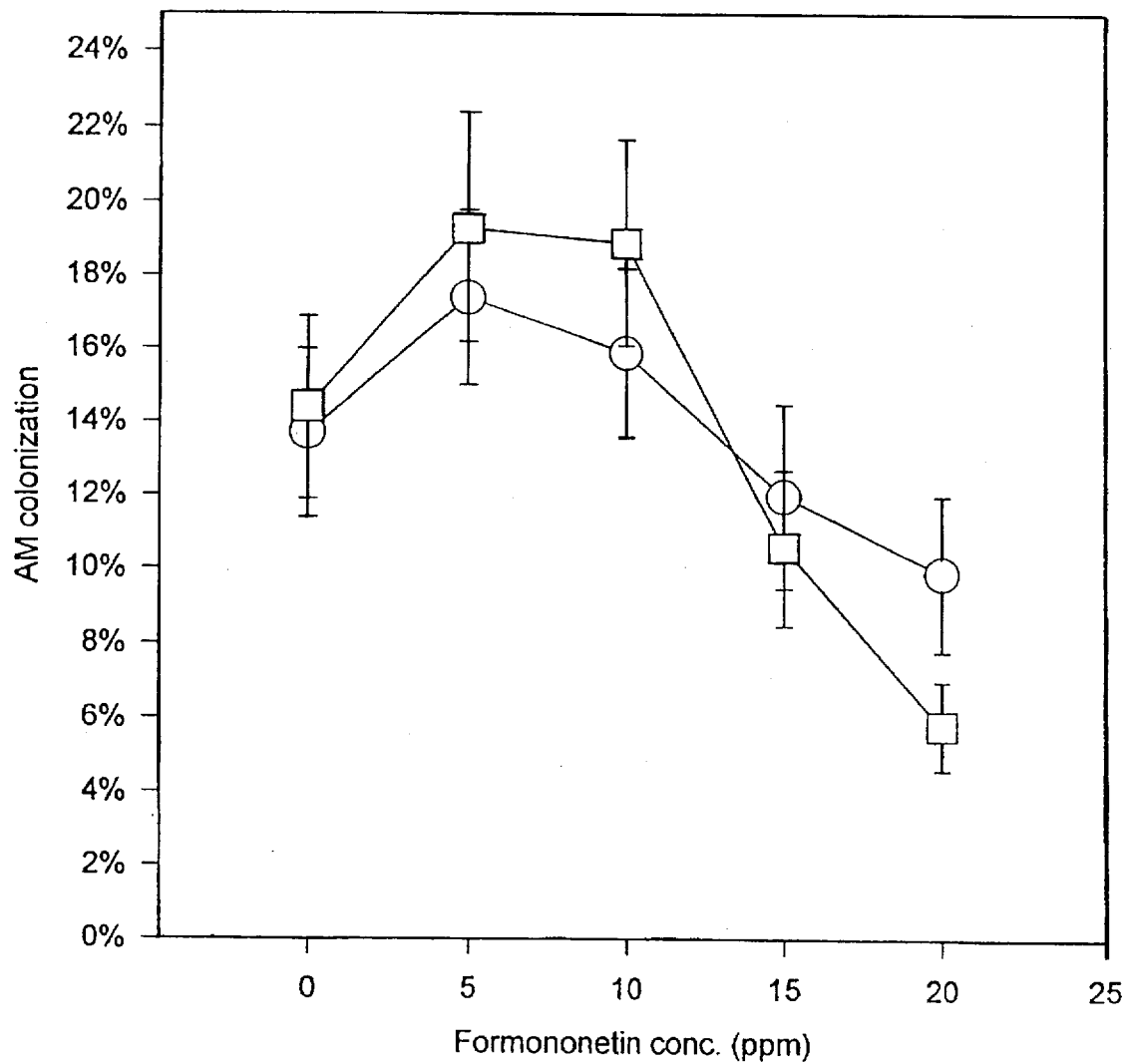
FIG. 1 is a graph showing the colonization of clover after four (4) weeks of growth in the presence of formononetin (O) and potassium formononetin (□). Bars indicate standard error.

The present invention relates to a composition useful for stimulating the growth of vesicular arbuscular mycorrhizal (VAM) fungi in the presence of a plant which comprises: an alkali metal formononetinate; and a plant material as a seed or propagule containing the compound as an additive in an amount which stimulates the growth of the VAM fungi which in turn stimulate growth of the plant material to a mature plant when the plant material is grown in a soil or a planting material in the presence of the VAM fungi.

The present invention also relates to an agricultural composition useful for stimulating the growth of plant material in the presence of vesicular arbuscular mycorrhizal (VAM) fungi which comprises an alkali metal formononetinate; and an agricultural carrier containing a dispersant which aids in dispersing the alkali metal formononetinate in soil or a planting material, wherein the alkali metal formononetinate is present in an amount between 0.1 and 400 parts per million by weight of the carrier and wherein the composition stimulates the growth of the VAM fungi which stimulate the growth of the plant material.

Further, the present invention relates to a method for growing vesicular-arbuscular mycorrhizal (VAM) fungi including spores of the fungi useful for stimulating plant growth which comprises: growing the VAM fungi in the presence of an amount of an alkali metal formononetinate added to the fungi so that the fungi produced are useful for stimulating the growth of the plant by being provided in soil with the plant during the growth.

Further still, the present invention relates to a fungal composition which comprises: vesicular-arbuscular mycorrhizal fungi which have been grown in the presence of an alkali metal formononetinate admixed with the fungus in absence of a plant which is to be stimulated by the fungi.

The present invention also relates to a fungal composition which comprises in admixture: an alkali metal formononetinate; and vesicular-arbuscular mycorrhizal fungi which are stimulated by the alkali metal formononetinate wherein the fungal composition is to be mixed with soil and stimulate the growth of a plant.

The present invention relates to a method for alleviating pesticide or herbicide injury to plants in a soil containing vesicular-arbuscular mycorrhizal fungi and containing the pesticides or herbicides at levels toxic to the plants which comprises growing the plant with the fungi in the presence of an alkali metal formononetin added to the soil.

The present invention relates to a method for stimulating the growth of a plant in culture which comprises: providing a plant or cells of the plant in a culture solution containing vesicular-arbuscular mycorrhizal fungi and an alkali metal formononetinate; and growing the plant in the culture solution.

Finally, the present invention relates to an alkali metal formononetinate, particularly potassium or sodium formononetinate alone or in combination. The compound has the structural formula:

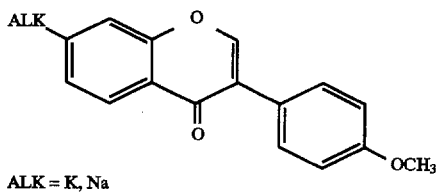

ALK = K, Na

The alkali metal formononetinates (AMF), particularly sodium and potassium, are soluble in water. The solubility is more than one (1) gram per ml which is unexpected. Other alkali metal salts which can be used are lithium, rubidium and casium salts, which are not preferred because of cost considerations.

The plant material can be rooted plants or plant tissue cells, organs, seeds or other parts of the plant and can be grown in culture with the VAM fungi. The preferred plant materials are corn, soybean, sorghum, asparagus, leek, onion, Taxus sp. and other woody species, coffee, clover, citrus, sea oats, wheat, potatoes and other crop plants, particularly those plants having roots which are colonized by the VAM fungi. The AMF is used in an amount between about 0.1 and 400 ppm in soil or planting mixes and can be used with fertilizers such as urea. Planting mixes can include vermiculite, polystyrene beads, peat moss and other fillers and growth factors. In tissue culture, the alkali metal formononetinate (AMF) is present in an amount between about 0.0001 and 400 ppm with the plant material and VAM fungi.

The AMF can be applied to the soil or planting mix either before or after the plants are planted. Preferably the AMF is applied at the time of planting of the seed. The VAM fungi can also be applied or they can be naturally present in the soil.

The AMF can be applied to the plant material, e.g. either to the seed or a propagule. Preferably the AMF is coated on the seed using an adhesive such as methyl cellulose, which is compatible with plant growth. The AMF can also be impregnated into the seed. Preferably the VAM fungi and seeds coated with the AMF are applied together. The VAM fungi can also be cultured with the AMF.

The preferred VAM fungi are in the genus Glomus such as *G. fasciculatum*, *G. intraradices* and *G. etunicatum*. These VAM fungi are particularly important commercially. It is preferred that the VAM fungi are grown in the presence of the AMF in an amount between about 0.0001 and 400 ppm in a culture medium. The culture medium contains sources of carbon, nitrogen, minerals and vitamins for the VAM fungi as is known to those skilled in the art.

The AMF can be applied in a liquid agricultural carrier with a dispersant which maintains the AMF in solution in an amount between about 0.1 and 400 micrograms per ml. Preferred dispersants are lower alkanols, particularly methanol, with various surfactants including anionic and cationic surfactants. The AMF can be provided in a solid mixture including the dispersant and the AMF. The composition can be formulated in solid carriers which aid in dispersing the AMF in the soil or planting material. The AMF is present in an amount between about 0.1 and 400 ppm by weight of the solid carrier.

The AMF can be formulated as wettable powders, flow concentrates, emulsifiable concentrates, granular formulations and the like.

Wettable powders can be prepared by grinding together about 20% to 45% by weight of a finely divided carrier such as a fertilizer (urea and NPK mixtures, nitrogen, phosphorus and potassium), kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water. Liquid fertilizers (NPK) and/or urea can be added.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the AMF is used for soil treatment, the compounds may be prepared and applied as granular products. Preparation of the granular product can be achieved by dissolving the active compound in a solvent such as water, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier. The composition can contain fertilizers such as urea and NPK fertilizers, by coating or admixing.

The AMF can also be mixed with a herbicide or pesticide which is applied to the plants or applied before or after the application of the herbicide or pesticide. The VAM fungi function as a "safener" in the presence of the AMF and overcome injury caused by the herbicides or pesticides. Injury caused by imidazolinone herbicides, such as imazaquin and imazethapyr, and pendimethalin can be overcome by the method of the present invention. Best results can be achieved when the composition is applied the year following a herbicide application to fields showing residual levels of herbicide sufficient to cause injury to crops planted into the field.

In the following Examples 1 to 3, a sterile 50/50 sand/soil mix was inoculated with a pot culture of *Glomus intraradices* to a homogeneous concentration of 0.5 spores/g. For VAM colonization assessment, the roots from each experiment were washed carefully. The roots were cleared and stained (Phillips, J. M. and D. S. Hayman, Trans. Brit. Mycol. Soc. 55:158–161 (1970)), and evaluated for AM colonization using the line intersect method (Kormanik, P. P. and A. C. McGraw, Quantification of vesicular-arbuscular mycorrhizae in plant roots, in: N. C. Schenck (ed.) Methods and principles of mycorrhizal research. APS Press, St. Paul, Minn. p. 37–45 (1982)).

EXAMPLE 1

A. Prior Art Compound

Formononetin was first dissolved in a small amount of hot methanol and then dissolved in water to make a stock solution of 20 ppm formononetin. The applied solutions were made by serial dilution of this stock to 15, 10 and 5 ppm. A control solution not containing the formononetin (0 ppm) was prepared.

B. New Compound

Formononetin (64 mg) was stirred with potassium hydroxide (KOH) (91 mg) and 10 ml of water. The resulting clear solution had a pH of about 8.0. This solution was lyophilized to yield a white powder. The potassium salt of formononetin was first dissolved in a small amount of water and then dissolved in water to make a stock solution of 20 ppm formononetin. Methanol was added to equal the amount used in the dissolution of the conventional formulation of formononetin. The methanol was added only to make the experiment comparable and is unnecessary because of the solubility of potassium formononetinate. The applied solutions were made by serial dilution of this stock to 15, 10 and 5 ppm. A control solution not containing the novel formulation of formononetin (0 ppm) was prepared.

Small (50 ml) plastic pots were filled with the inoculated sand/soil mix. Twelve pots were used for each treatment. The soil in each pot was wetted with 20 ml of the appropriate solution. Approximately 12 white clover (*Trifolium repens*) seeds were placed in each pot and pushed below the surface. The pots were arranged in a greenhouse and grown under natural light supplemented with halogen grow lights for 14 hours/day. The pots were bottom-watered for 4 weeks. No nutrition was applied. After 4 weeks, the soil was washed from the roots and the tops were removed. The data is shown in FIG. 1 where (O) is formononetin and (□) is potassium formononetinate.

EXAMPLE 2

A formulation of formononetin (A) was first dissolved in a small amount of hot methanol and then dissolved in water to make a stock solution of 10 ppm formononetin (½ of Example 2). The applied solutions were made by serial dilution of this stock to 8, 6, 4 and 2 ppm. A control solution not containing the conventional formulation of formononetin (0 ppm) was prepared.

The potassium salt of formononetin of Example 1 was first dissolved in water to make a stock solution of 10 ppm potassium formononetinate. Methanol was added to equal the amount used in the dissolution of the formulation of formononetin. The applied solutions were made by serial dilution of this stock to 8, 6, 4 and 2 ppm. A control solution not containing the potassium formulation of formononetin (0 ppm) was prepared.

Small (50 ml) plastic pots were filled with the inoculated sand/soil mix. Twelve pots were used for each treatment. The soil in each pot was wetted with 20 ml of the appropriate solution. Approximately 12 white clover (*Trifolium repens*) seeds were placed in each pot and pushed below the surface. The pots were arranged in a greenhouse and grown under natural light supplemented with halogen grow lights for 14 hours/day. The pots were bottom-watered for 4 weeks. No nutrition was applied. After 4 weeks, the soil was washed from the roots and the tops were removed. The data is also shown in FIG. 1 where the (O) is formononetin and (□) is potassium formononetin.

EXAMPLE 3

Prior art compound

Formononetin was first dissolved in a small amount of hot methanol and then dissolved in water to make a stock solution of 10 ppm formononetin. The applied solutions were made by serial dilution of this stock to 8, 6, 4 and 2 ppm. A control solution not containing the formulation of formononetin (0 ppm) was prepared.

New Compound

The potassium salt of formononetin was dissolved in water to make a stock solution of 10 ppm potassium formononetinate. Methanol was added to equal the amount used in the dissolution of the conventional formulation of formononetin. The applied solutions were made by serial dilution of this stock to 8, 6, 4 and 2 ppm. A control solution not containing the novel formulation of formononetin (0 ppm) was prepared.

Medium (200 ml) plastic pots were filled with the inoculated sand/soil mix. Twelve pots were used for each treatment. The soil in each pot was wetted with 40 ml of the appropriate solution. Corn (*Zea mays*) seeds were pregerminated for 36 hours in the dark. One seed was placed in each pot and pushed below the surface. The pots were arranged in a greenhouse and grown under natural light supplemented with halogen grow lights for 14 hours/day. The pots were bottom-watered for 5 weeks. No nutrition was applied. After 5 weeks, the soil was washed from the roots and the tops were removed. The results were that the root colonization by the VAM was significantly increased (20% more than formononetin).

EXAMPLE 4

An experiment was performed with *Taxus X densiformis* and *Taxus X hicksii* to determine root colonization with potassium formononetinate in three separate media.

Figure 2:
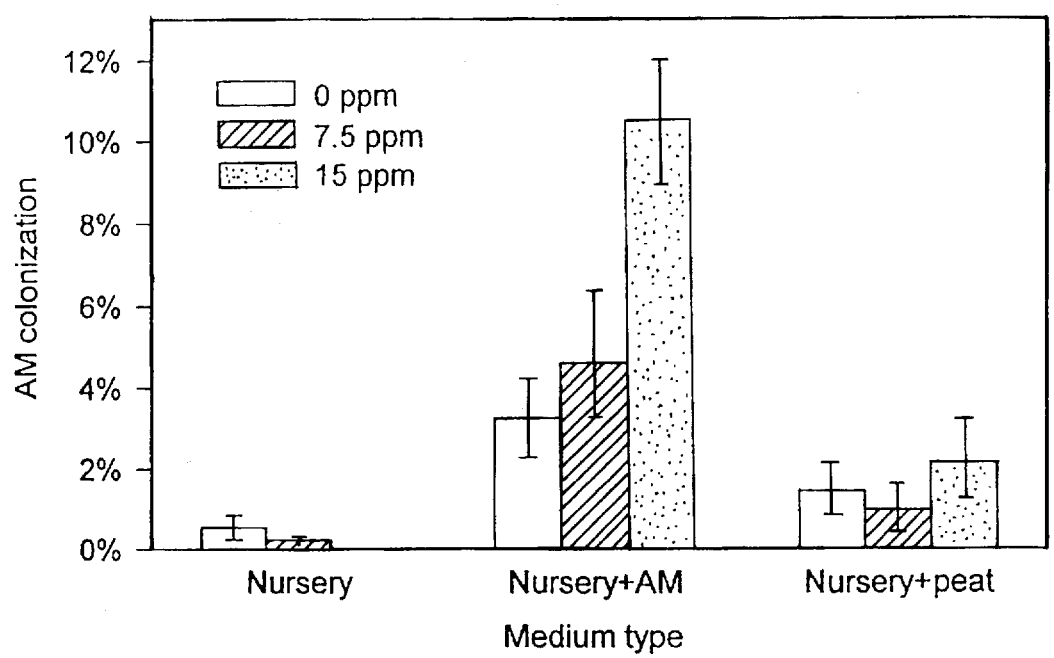
FIGS. 2 and 3 are graphs showing the colonization of *Taxus X densiformis* and *Taxus X hicksii* on three growth media as a function of concentration of potassium formononetin. Vertical bars indicate standard error.
Figure 3:
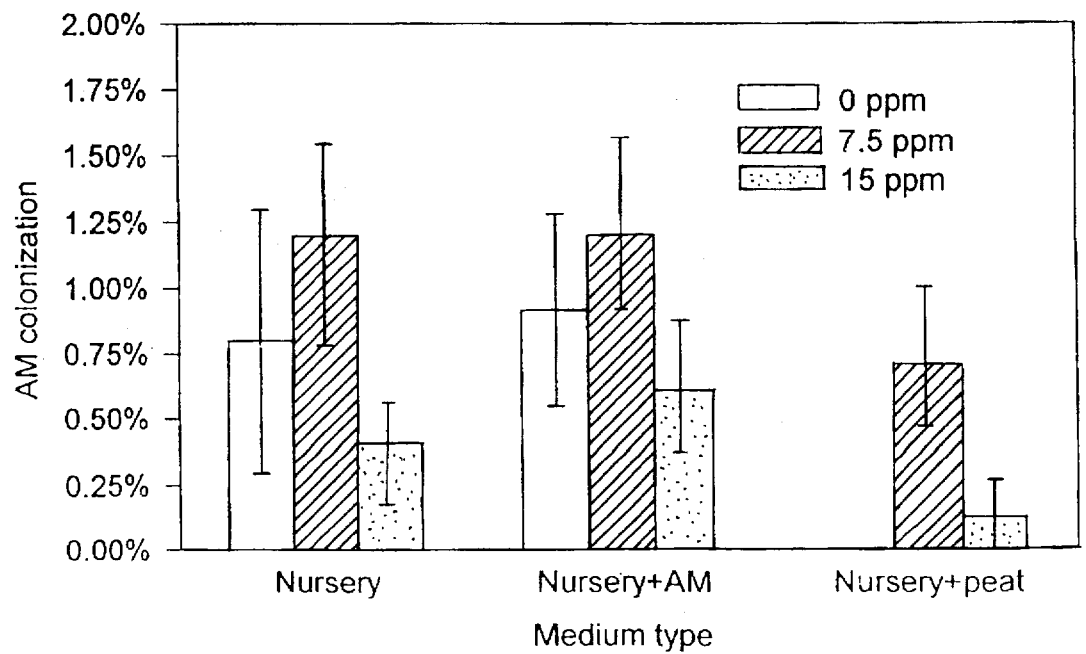

Rooted cuttings of *Taxus X densiformis* and *Taxus X Hicksii* were obtained from Lincoln Nurseries, Grand Rapids, Mich. Cuttings were individually planted into plastic cells (6 cm×6 cm×12.8 cm) containing one of three prepared mixes. Metro Mix 510 (Scott Sierra Horticultural Products, Marysville, Ohio) was used as a standard nursery growing medium. Metro Mix 510 contains composted pine bark, vermiculite, Canadian sphagnum peat moss, processed bark ash, washed sand and wetting agent. Mycorrhizal treatment was obtained from Mycori Mix (Sogevex Inc., Red Hill, Pa. and Le Tourbieres Premier Ltee., Riviere-du-Loup, Quebec). It contains Canadian sphagnum peat moss, perlite, vermiculite, Glomus inraradix inoculant, calcitic and dolomitic lime, and a wetting agent. SB-Mix (Sogevex Inc., Red Hill, Pa. and Le Tourbieres Premier Ltee., Riviere-du-Loup, Quebec) was used as a control for the Mycorrhizal treatment. It contains the same ingredients as Mycori Mix without the Glomus intraradix inoculant. The planting media were as follows: Medium #1, 100% Metro Mix 510; Medium #2, 50% Metro Mix 510 and 50% Mycori Mix (v/v); Medium #3, 50% Metro Mix 510+50% SB-Mix (v/v). Plants were placed in a glass greenhouse and watered to thoroughly moisten the planting media. Potassium formononetinate treatments were applied following the initial wetting of the media. Potassium formononetinate solution was prepared using distilled water. Treatment rates consisting of 0 ppm (distilled water only), 7.5 ppm, and 15.0 ppm. Each plant received 20 ml of the appropriate treatment solution. During the course of the experiment the Taxus plants were watered as needed to maintain adequate media moisture and fertilized weekly with 100 ppm nitrogen using Peters professional Fertilizer 20-10-20 (nitrogen-phosphorus-potassium). The experiment began on 7 Jun. 1995 and was terminated on 19 Sep. 1995. Taxus cultivars were evaluated in separate experiments as follows: 3 media×3 potassium formononetinate rates×5 replicates, with 3 plants per replicate. Fifteen plants per treatment combination were used to evaluate root colonization by VAM. The results are shown in FIGS. 2 and 3 and in Table 2.

TABLE 2

| Treatments | Nursery (Medium 1) | Nurs + VAM (Medium 2) | Nurs + Peat (Medium 3) |
|---|---|---|---|
| 0 ppm (Form 1) | Treat. 1 | Treat. 2 | Treat. 3 |
| 7.5 ppm (Form 2) | Treat. 4 | Treat. 5 | Treat. 6 |
| 15 ppm (Form 3) | Treat. 7 | Treat. 8 | Treat. 9 |

| Medium | Treatment No. | Potassium Salt conc. (ppm) | *Taxus x densiformis* Colonization %[a] | *Taxus x hicksii* Colonization % |
|---|---|---|---|---|
| Nursery | 1 | 0.0 | 0.543 a | 0.794 abc |
|  | 4 | 7.5 | 0.128 a | 1.199 c |
|  | 7 | 15.0 | 0.000 a | 0.398 abc |
| Nursery + VAM | 2 | 0.0 | 3.267 bc | 0.913 bc |
|  | 5 | 7.5 | 4.615 c | 1.201 c |
|  | 8 | 15.0 | 10.483 d | 0.604 abc |
| Nursery + Peat | 3 | 0.0 | 1.433 ab | 0.000 a |
|  | 6 | 7.5 | 0.975 ab | 0.704 abc |
|  | 9 | 15.0 | 2.161 abc | 0.134 ab |

[a]Letters in a given column with different letters are significantly different (P ≦ 0.05).

As can be seen, the results show that the colonization is increased depending upon the amount of the potassium formononetin.

It is intended that the foregoing description be only illustrative of the present invention and that the present invention be limited only by the hereinafter appended claims.

We claim:

1. A composition useful for stimulating the growth of VAM fungi in the presence of a plant which comprises:
   (a) an alkali metal formononetinate; and
   (b) a plant material as a seed or propagule containing the compound as an additive in an amount which stimulates the growth of the VAM fungi which in turn stimulate growth of the plant material to a mature plant when the plant material is grown in a soil or a planting material in the presence of the VAM fungi.

2. An agricultural composition useful for stimulating the growth of plant material in the presence of vesicular arbuscular mycorrhizal (VAM) fungi which comprises:

(a) alkali metal formononetinate; and (b) an agricultural carrier containing a dispersant which aids in dispersing the alkali metal formononetinate in soil or a planting material, wherein the alkali metal formononetinate is present in an amount between 0.1 and 400 parts per million by weight of the carrier and wherein the composition stimulates the growth of the VAM fungi which stimulate the growth of the plant material.

3. A method for growing vesicular-arbuscular mycorrhizal (VAM) fungi including spores of the fungi useful for stimulating plant growth which comprises:

growing the VAM fungi in the presence of an amount of an alkali metal formononetinate added to the fungi so that the fungi produced are useful for stimulating the growth of the plant by being provided in soil with the plant during the growth.

4. The method of claim 3 wherein the fungi are selected from the group consisting of fungi which colonize roots of the plant.

5. The method of claim 3 wherein an amount of the alkali metal formononetinate between about 0.1 and 400 ppm is provided in a medium for growing the fungi.

6. The method of claim 5 wherein the medium contains a source of carbon, nitrogen and vitamins and minerals which stimulate the growth of the fungi.

7. The method of claim 5 wherein the medium contains plant materials which stimulate growth of the fungi.

8. The method of claim 5 wherein the medium contains a source of carbon, nitrogen and vitamins and minerals which stimulate the growth of the fungi and wherein the medium contains plant materials which stimulate growth of the fungi.

9. A fungal composition which comprises:

vesicular-arbuscular mycorrhizal fungi which have been grown in the presence of an alkali metal formononetinate admixed with the fungus in absence of a plant which is to be stimulated by the fungi.

10. A fungal composition which comprises in admixture:

(a) an alkali metal formononetinate; and (b) vesicular-arbuscular mycorrhizal fungi which are stimulated by the alkali metal formononetinate wherein the fungal composition is to be mixed with soil and stimulate the growth of a plant.

11. The composition of claim 10 wherein the fungi are admixed with a plant material.

12. A method for alleviating pesticide or herbicide injury to plants in a soil containing vesicular-arbuscular mycorrhizal fungi and containing the pesticides or herbicides at levels toxic to the plants which comprises growing the plant with the fungi in the presence of an alkali metal formononetinate added to the soil.

13. In a method for stimulating the growth of a plant material in the presence of vesicular-arbuscular mycorrhizal fungi, the improvement which comprises:

growing the plant material with the fungi in the presence of an alkali metal formononetinate.

14. The method of claim 13 wherein the alkali metal formononetinate is applied in an amount between about 0.1 and 400 ppm in the soil or planting mixes.

15. The method of claim 14 wherein the fungi are applied with the alkali metal formononetinate.

16. The method of claim 13 wherein the plant is selected from the group consisting of plants having roots colonized by these fungi.

17. The method of claim 13 wherein a seed or a propagule is planted and the alkali metal formononetinate is applied at about the time of the planting.

18. The method of claim 17 wherein the seed or a propagule is coated with the alkali metal formononetinate.

19. A method for stimulating the growth of a plant in culture which comprises:

(a) providing a plant or cells of the plant in a culture solution containing vesicular-arbuscular mycorrhizal fungi and an alkali metal formononetinate; and (b) growing the plant in the culture solution.

20. The method of claim 19 wherein the plant is colonized by the fungi.

21. The method of claim 19 wherein the amount of the alkali metal formononetinate is between about 0.1 and 400 ppm in the solution.

22. The composition of claim 1 wherein the alkali metal is potassium.

23. The composition of claim 2 wherein the alkali metal is potassium.

24. The composition of claim 10 wherein the alkali metal is potassium.

25. The method of claim 3 wherein the alkali metal is potassium.

26. The method of claim 12, wherein the alkali metal is potassium.

27. The method of claim 19, wherein the alkali metal is potassium.

28. An alkali metal formononetinate.

29. Potassium formononetinate.

30. Sodium formononetinate.

* * * * *